United States Patent [19]

Bailey, Jr. et al.

[11] Patent Number: 4,870,964
[45] Date of Patent: Oct. 3, 1989

[54] OPTHALMIC SURGICAL DEVICE AND METHOD WITH IMAGE DATA REFLECTED OFF OF THE EYE

[75] Inventors: Paul F. Bailey, Jr., 4885 NW. Barnes Rd., Portland, Oreg. 97210; Isidro G. Nilsson, Marysville; George M. Alf, Everett, both of Wash.

[73] Assignee: Paul F. Bailey, Jr., Portland, Oreg.

[21] Appl. No.: 207,545

[22] Filed: Jun. 16, 1988

[51] Int. Cl.$^4$ ............................................. A61B 17/36
[52] U.S. Cl. .................................. 128/303.1; 351/211
[58] Field of Search ...................... 128/303.1, 395–398, 128/303 R, 316, 633; 350/110; 351/211, 237; 354/62, 127.1, 273; 433/27

[56] References Cited

U.S. PATENT DOCUMENTS

| | | | |
|---|---|---|---|
| 3,499,715 | 3/1970 | Hanson et al. | 350/110 |
| 3,613,666 | 10/1971 | Hobbs | 128/649 |
| 3,812,855 | 5/1974 | Banko | 128/276 |
| 3,832,042 | 8/1974 | Heine | 351/6 |
| 3,860,000 | 1/1975 | Wootten et al. | 128/230 |
| 3,950,775 | 4/1976 | Toyama et al. | 354/273 |
| 3,990,452 | 11/1976 | Murry et al. | 128/305 |
| 4,024,866 | 5/1977 | Wallach | 128/276 |
| 4,117,843 | 10/1978 | Banko | 128/230 |
| 4,168,707 | 9/1979 | Douvas et al. | 128/276 |
| 4,180,074 | 12/1979 | Murry et al. | 128/276 |
| 4,184,510 | 1/1980 | Murry et al. | 137/565 |
| 4,248,496 | 2/1981 | Akin, Jr., et al. | 350/10 |
| 4,261,360 | 4/1981 | Perez | 128/230 |
| 4,378,014 | 3/1983 | Elkow | 128/214 |
| 4,378,797 | 4/1983 | Osterholm | 604/24 |

Primary Examiner—Max Hindenburg
Attorney, Agent, or Firm—Kolisch, Hartwell & Dickinson

[57] ABSTRACT

Method and apparatus providing to a medical practitioner visual feedback of information revelant to a surgical or therapeutic procedure are described. Vacuum and pressure conditions are sensed by a "T" section tap onto the aspiration and irrigation lines of conventional equipment. Ultrasonic power level also is sensed, by electronic means responsive to conventional emulsification equipment. The signals produced thereby are processed to produce an image the reflection of which off the patient's cornea is visible to the surgeon and interpretable by the surgeon as indicative of the conditions. Processing and imaging means convert the analog signals to a digital code used to modulate the various elements of a circularly arrayed, plural element light source. The processing and imaging electronics are contained within a light array housing connected at the end of a freestanding, flexible, gooseneck lamp fixture. The housing may be manipulated by the surgeon or an assistant to produce a preferred image size, location and intensity. In a proposed modification, color modulation is used to produce the image. In another modification, a fiber optic cable bundle is used to produce the image, the bundle conveying light from a source located, with the imaging electronics, in the base of the fixture. In yet another modification, the lights in the array visibly are cycled on and off to indicate that the emulsifier is operating. In a final modification, various alternative imaging patterns are proposed. In a final modification, the image is projected onto any visible region of the patient's body.

9 Claims, 2 Drawing Sheets

OPTHALMIC SURGICAL DEVICE AND METHOD WITH IMAGE DATA REFLECTED OFF OF THE EYE

BACKGROUND OF THE INVENTION

This invention relates generally to a display monitor system for use in surgery or therapy, and more particularly to method and apparatus for providing an ophthalmic surgeon with the ability perpetually to monitor equipment status without diverting attention from the eye surgery by reflecting a coded visual image off of the cornea of the patient's eye. The preferred embodiment of the invention is described in the context of conventional aspiration, irrigation and phacoemulsification equipment used in cataract extraction surgery.

Heads up display systems presently are being used in aircraft instrumentation, whereby a pilot is provided simultaneously with a direct view of the path ahead of the aircraft and an indirect view, e.g. a projection onto the aircraft's windshield, of the status of critical aircraft equipment parameters. In this way, the pilot need not divert attention, even momentarily, from the immediate flight path in order also to monitor equipment and environmental parameters equally critical to reaching a destination. It is felt that, with regard to providing an aircraft pilot with information—especially during critical maneuvers—more is better.

Prevention of anterior chamber collapse during an ophthalmic surgical procedure requires not only the skill and dexterity, but also the close attention, of an experienced surgeon. Conventional aspiration, irrigation and emulsification equipment provide a front panel indication of such parameters as vacuum, pressure, and ultrasonic power level; and elapsed time, all of which must be closely monitored by the surgeon. In cataract extraction surgery, the surgeon simultaneously must manipulate two hand tools (one tool in each hand), one having an irrigation needle and the other having an aspiration needle and emulsification means (or one coaxial assembly which can provide irrigation, aspiration and emulsification and can be manipulated by one hand). Clearly, this is no time for the surgeon to divert attention from the field of operation, as is required by conventional monitoring equipment, especially during unassisted operation. Audible alarms, such as beepers, provide a distracting and imprecise form of feedback It is desirable to provide 'heads up,' or perpetual, display monitor method and apparatus for use in opthalmic surgery that supplies the surgeon with any needed information regarding the condition of patient, eye or equipment, or other data pertinent to the procedure, without diverting the surgeon's attention from the region of the patient's eye. Because of the variety of data that has been found to be helpful in performing the surgery, the method and apparatus should be versatile enough to convey a large amount of information Because much of the information will regard conditions responsive to actions taken by the surgeon, and because minute delay can produce disastrous consequences, the method and apparatus should be able to provide feedback in real time response to those actions of the surgeon that are capable of affecting such conditions. Preferably, the method and apparatus would be easily adaptable to a wide range of conventional techniques and equipment, requiring little or no modification thereto.

Accordingly, it is a principal object of the present invention to provide a display monitor system that may be viewed by a surgeon without diverting the surgeon's attention away from the situs of the procedure being performed. Other important objects of the invention include the following:

(1) to provide a versatile system adaptable to a wide range of uses in providing constructive feedback to the surgeon;

(2) to provide a system, as described, that unobtrusively, but clearly, conveys information to the surgeon regarding the condition of patient, eye or external equipment;

(3) to provide a system the use of which requires little or no modification to existing techniques or equipment;

(4) to provide a system the image projecting part of which is lightweight, portable and easily manipulated by the surgeon;

(5) to provide a system the use of which relatively easily and quickly may be learned; and (6) to provide a system that is reliable and inexpensive to use.

SUMMARY OF THE INVENTION

Method and apparatus are described that produce an image, which is interpretable by the surgeon as indicative of relevant data monitored by external equipment, on a visible region of the patient's eye for visual monitoring by the surgeon. In the preferred method of the invention, the image is produce by modulating a visible light source with the data and reflecting the modulated light source off of the patient's cornea. More specifically, predefined conditions responsive to the surgical procedure are sensed, e.g. by conventional, external equipment, to produce a signal representative of the condition, and the signal is processed to produce the visual image. Apparatus are described in which the vacuum pressure line of an aspirating unit is tapped with a "T" section, providing a measure of the dry or liquid vacuum condition of the line to produce an analog signal which varies proportionally therewith; the analog signal is digitized to produce a 10-bit coded output; and the digital output is conditioned to drive ten circularly arrayed, incandescent light bulbs By the preferred method of the invention, adjacent lights in the circular array progressively are turned on as the vacuum within the aspiration line increases, with, for example, no lights indicating a minimum vacuum level and a full circle of lights indicating a maximum vacuum level The light array is positioned, relative to the patient and the surgeon such that the reflection of the light array's image off of the patient's cornea is perpetually viewable by the surgeon.

In a proposed modification to the preferred method of the invention, a colored light array is modulated by the data to provide a color coded image which is interpretable as indicating a variety of prevailing conditions In a proposed modification to the preferred embodiment, the light array comprises a fiber optic cable, or light tube bundle, which may be arranged within a freestanding, flexible, gooseneck fixture the base of which houses the processing and imaging electronics This embodiment renders the light array more easily manipulated by the surgeon, while maintaining its position once oriented. In yet another proposed modification, at least one of the lights in a plural element array visibly and repeatedly may be cycled on and off to provide a blinking indication that the ultrasonic emulsifier is operating. In a series of further proposed modifications, various alternative imaging patterns are described, demonstrating the applicability and versatility of the novel method and apparatus. In a final proposed modification, a visible image is projected onto any visible region of the patient's body.

Thus, the various objects of the invention are achieved An unobtrusive, but clear, visual image is produced on the cornea of the patient's eye, the image being interpretable by the surgeon as indicative of a number of conditions relevant to the surgical procedure being performed. In its preferred embodiment, the apparatus is structured such that it is easily adapted, by simple "T" sections, to vacuum and pressure lines of conventional equipment Similarly, by virtue of the freestanding feature of the light array fixture, no modification whatsoever is required to the variety of microscopes which may be used in such procedures. Conventional, solid state circuitry is used for data processing and imaging, thereby providing reliable, low cost operation. In summary, the versatile 'heads up' display system described herein may be used to provide perpetual, visual feedback of a wide range of desirable information including, but not limited to, vacuum or pressure level, power level, flow rate, emulsifier on/off condition, and elapsed time, thereby potentially significantly improving the precision and safety of ophthalmic surgery.

These and other objects and advantages of the present invention more clearly will be understood from consideration of the drawings and the following description of the preferred embodiment.

DETAILED DESCRIPTION OF THE PREFERRED EMBODIMENT

Figure 1:
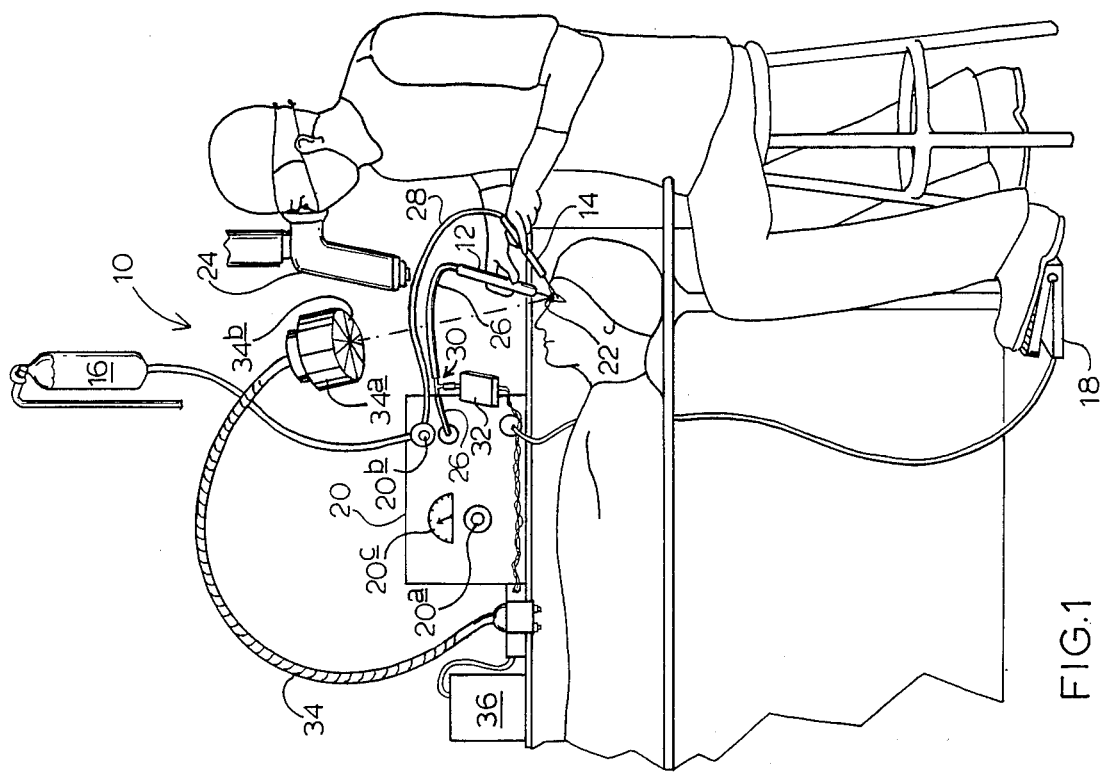
FIG. 1 shows the use of the perpetual display monitor system made in accordance with the preferred embodiment of the invention

Referring first to FIG. 1, the perpetual display monitor system, in its preferred embodiment, is indicated generally at 10. The display monitor system is illustrated as it might be used in ophthalmic surgery performed by a surgeon on a patient, whose human forms are shown for the purpose of illustrating their interaction with the system. The (supine) patient is shown undergoing a surgical technique that involves the ultrasonic emulsification of a cataractous lens, and the aspiration of fluid, lens and cortex material from an anterior, intraocular chamber by the use of a hand tool 12, shown held in the (seated) surgeon's right hand. The surgeon's left hand is shown holding an irrigation hand tool 14, which provides for the gravity fed, rate controlled, simultaneous introduction of saline solution 16 into the anterior chamber of the patient's eye. The surgeon's left foot works a foot pedal 18, which controls the aspiration vacuum level produced by conventional irrigation/aspiration (IA) equipment 20. Preferably continuously throughout the procedure, the surgeon views a region immediately surrounding the patient's affected eye 22, as will be described in reference to FIG. 2, through a microscope 24.

IA equipment 20, which forms no part of the present invention, typically is capable of at least one of aspirating and irrigating a patient's intraocular chamber by fluid communicating therewith, via vacuum line 26 and pressure line 28 and via hand tools 12, 14, a respectively lower and higher pressure condition than the pressure within the chamber. Typically, IA equipment 20 provides controls, such as dials 20a, 20b and indicators, such as meter 20c, for setting ultrasonic power, vacuum and pressure levels and for providing the surgeon with feedback, regarding the instantaneous vacuum being supplied by the equipment's pump, responsive to the application of pressure on foot pedal 18. Because the surgeon's attention is properly focused on the patient's eye, rather than on the front panel indicators of IA equipment 20, more advanced IA equipment provides an audible alarm to the surgeon upon the occurrence of certain predefined events, e g , when a prescribed vacuum level is exceeded With reference still to FIG. 1, the features and advantages of perpetual display monitor system 10 generally are described. System 10 comprises means for sensing a lower or higher than intraocular pressure condition in a vacuum or pressure line, such as line 26, to produce a signal which is representative of the pressure condition; means for processing the signal to produce a visible image interpretable by the surgeon as being indicative of the pressure condition; and means for positioning the image relative to the surgeon and the patient's eye such that the image visibly is reflected off of a visible region of eye 22 for perpetual monitoring, through microscope 24, by the surgeon. Thus, display monitor system 10 provides a surgeon with a perpetual indication of desirably monitored conditions incident to the surgery, without requiring the surgeon to divert attention from the site of the surgery.

In the preferred embodiment of the invention, sensing means takes the form of a tap 30, which taps vacuum line 26, and a signal conditioner 32. The conditioned signal then is routed to signal processing means located within the display head 34a of a freestanding lamp fixture 34. It will be appreciated that fixture 34 may assume any useful form such as a flexible, ultra-lightweight fiber optic cable bundle, wherein an incandescent or luminescent light source is located, along with associated sense, decode and drive electronics, in a remote housing, e.g. that of signal conditioner 32. By straightforward means, which will be described in reference to FIG. 3, the analog signal from conditioner 32 is converted to a digital signal for driving a circular, ten element light array 34b. Not shown in FIG. 1 is ultrasonic detection means, preferably located within display head 34a, which, by well known band-pass filtering and amplification techniques, will detect ultrasonic emanations (typically 40 kHz) from IA equipment 20 when the ultrasonic emulsifier is on. As will be described in reference to FIG. 5, this on/off condition of the emulsifier also may be coded into light array 34b, thereby to provide the surgeon with visual feedback as to when the emulsifier is operating. It will be appreciated that alternative means for sensing any number of conditions useful to the surgeon may be provided, e.g. if IA equipment 20 provides for monitoring by external equipment, then some or all of transducer 30, signal conditioner 32 and ultrasonic detection means will be obviated, and the available outputs may be directly connected to signal processing means for driving light array 34b. Finally regarding FIG. 1 a DC power source 36 is provided, which in the preferred embodiment provides 13.8 V to electronic circuitry within signal conditioner 32 and display head 34a.

Figure 2A:
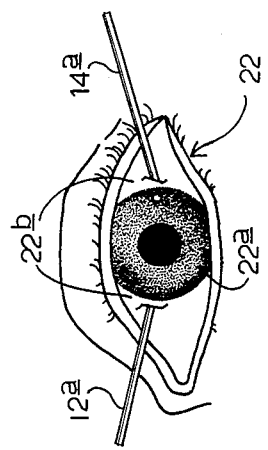
FIGS. 2A-2D illustrates, in selected phases of operation, image production on the cornea of the patient's eye.

Referring briefly now to FIG. 2, it will be seen how perpetual display monitor system 10 usefully may be employed by the surgeon in cataract surgery FIGS. 2A through 2D represent what may be thought of as a 'surgeon's-eye' view of the patient's eye in which an aspiration/emulsification needle, or cannula, 12a is shown inserted through a first corneal incision on one side of the sclera, and an irrigation needle, or cannula, 14a, is shown inserted through a second corneal incision on the opposite side of the sclera As will become apparent, FIG. 2A shows a phase of the ophthalmic surgery in which no vacuum is being produced in aspiration line 26, and, correspondingly, no elements of light array 34b are visible on cornea 22a. In the preferred embodiment of the invention, an imaging pattern in which none of the ten elements of light array 34b is on corresponds to a condition of equipment 20 in which the vacuum in aspiration line 26 is determined to be at a negligibly low level. Thus, the surgeon would interpret this particular image on cornea 22a as indicative of a negligible vacuum level, responsive to little or no pressure on foot pedal 18.

FIG. 2 illustrates the visual results of progressively increased pressure on foot pedal 18. In FIG. 2B, a small light spot is clearly visible, in the region of the iris, on cornea 22a of eye 22. A familiar user of display monitor system 10 interprets this pattern as indicating that a relatively low level vacuum is being produced by IA equipment 20. FIG. 2C indicates a vacuum level which, by the one half completion of a circle of light spots, is approximately one half a predetermined maximum. Finally, FIG. 2D shows a completed circle of ten light spots, corresponding to the ten elements of light array 34b, indicating a maximum vacuum level of IA equipment 20.

While tactile feedback from foot pedal 18 marginally indicates to the surgeon the position of foot pedal 18, the image visible on cornea 22a importantly provides the surgeon with graphic evidence of the amount of vacuum being delivered to the anterior chamber of eye 22. In other words, the perpetual display monitor system of the present invention equips the surgeon with quantitative, as well as qualitative, feedback regarding the actual vacuum level in aspiration line 26, rather than the position of a foot pedal Better yet, the surgeon may be perpetually so-informed while working hand tools 12, 14, pressing foot pedal 18 and gazing intently at eye 22.

It will be appreciated that any light coding convention may be adopted, and any image may be produced in the corneal region of the patient's eye, subject only to the physical constraints of the eye's imaging surface and the surgeon's ability readily to interpret the image produced thereon. As will be discussed in reference to FIG. 5, any one of numerous graphic, alphanumeric or mixed images may be produced at sufficient contrast ratio and resolution as to be visible to the surgeon. It will be appreciated that multiple conditions simultaneously may be imaged, further including but not limited to the pressure in pressure line 28, the on/off condition of the ultrasonic emulsifier, the elapsed time, the time of day or any other desirable information Finally, it will be appreciated that the image may be reflected off of any desired visible region of eye 22 by varying the angle of the incident axis between display head 34a and eye 22 (which axis is indicated in FIG. 1 by a dash-dot line), and that the image may be sized by varying the distance of display head 34a from eye 22 along that axis. While it may be possible to produce a visible image on a visible region of eye 22 other than cornea 22a, e.g. on the sclera 22b, it has been found that, with light array 34b, cornea 22a is a preferred imaging surface because it is of sufficient contrast with the reflected light spots to render the image readily discernable and interpretable. Of course, with more collimated (less diffuse) light sources, it will be possible, within the spirit of the invention, to project a visible image onto any desirable region of the patient's body, preferably a region immediately adjacent the focus of the medical practitioner's attention.

Figure 3:
FIG. 3 schematically illustrates the conditioning, processing and imaging electronics of the display monitor system.

Turning next to FIG. 3, the signal conditioning, processing and imaging electronics are illustrated as comprising signal conditioner 32 and signal processing means 38. Signal conditioner 32 includes pressure transducer 40, which may be powered by an 8 V, three terminal DC voltage regulator 42 and 0.1 $\mu$F decoupling capacitors C1, C2. In the preferred embodiment of the invention, transducer 40 is a temperature compensated, monolithic, differential pressure transducer having two pressure ports and a $\pm 30$ pounds per square inch (PSI) operating range, such as the LX06030D device available from SenSym, Inc of Sunnyvale, Calif. Those of ordinary skill in the art will appreciate that any transducer may be used which is capable of sensing absolute pressure at a single port or differential pressure between dual ports, and having good linearity over temperature, such devices being generally available for use in medical and automotive diagnostics and controls In the preferred embodiment, the differential transducer 40 outputs V+, V− are differenced and amplified through series resistors R1, R2, operational amplifier 44, and feedback resistor R3 in parallel with capacitor C3. The output of operational amplifier 44 feeds series resistor R4 and becomes the minus input to operational amplifier 46, the output ANALOG SENSE of which is fed back through GAIN CONTROL potentiometer K1. The plus input to operational amplifier 46 is a selectable, constant DC voltage within the range 0 V to 8 V that is produced by the wiper of a CENTERING CONTROL potentiometer K2. The adjustment of potentiometers K1, K2 will be described in detail below. In the preferred embodiment, desirable component values include: 10k ohms for R1, R2; 100K ohms for R3; 0.01 $\mu$F for C1; 1k ohms for R4; 50k ohms for K1, K2.

ANALOG SENSE is routed, along with DC power and ground, to signal processing means 38, which in the preferred embodiment is located within display head 34b ANALOG SENSE is connected to the input of a dot/bar display driver 48 the select input ("SEL") of which is connected to 13.8 V, thereby selecting the bar mode of driver 48. Driver 48 will be understood in this mode of operation to digitize the input, ANALOG SENSE, to produce on outputs D1 through D10 a 10-bit, binary, bar code wherein a successively higher or lower number of outputs are on in response to a progressively higher or lower analog input voltage, respectively.

In the preferred embodiment, driver 48 is implemented with an LM3914 device, which produces a linear coded output in which a minimum analog input is represented by (complementary) high outputs on D1 through D10, and in which a maximum analog input is represented by (complementary) low outputs thereon The upper and lower limits of the analog input which will be represented by all low and all high outputs, respectively, on D1 through D10, are set by connection of RLO and RHI through R5 to ground and through R7 to the 8 V output of a three terminal DC voltage regulator 50. In the preferred embodiment, R5 and R7 are of equal resistance, specifically 5.1k ohms, which corresponds to upper and lower limits of 6 V and 2 V as the dynamic range over which ANALOG SENSE may be expected to vary, as a linear function of vacuum. Resistor R6, which is connected between ground and the REF pin of driver 48 controls the amount of current at the outputs D1 through D10, and in the preferred embodiment is 1.2k ohms. D1 through D10 are connected to lamp drivers, such as lamp driver 52, which in the preferred embodiment comprises Darlington connected field effect transistors (FETs) configured as shown in a TIP116 package An incandescent lamp, such as lamp L1, is connected between the emitter of driver 52's output transistor and 13.8 V. In operation, as ANALOG SENSE varies over the linear operational output range of operational amplifier 46, between 2 V and 6 V, the array of ten lamps L1 (an exemplary one of which is shown in FIG. 3) are turned on and off by lamp drivers 52 (an exemplary one of which is shown in FIG. 3) in an incrementally increasing and decreasing number.

Figure 2B:
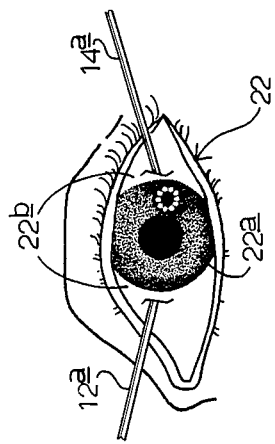
Figure 2C:
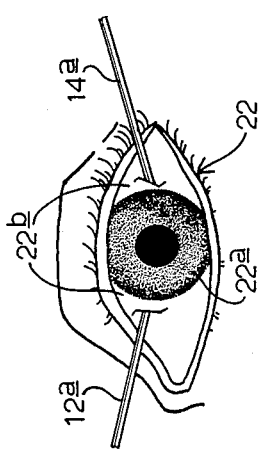
Figure 2D:
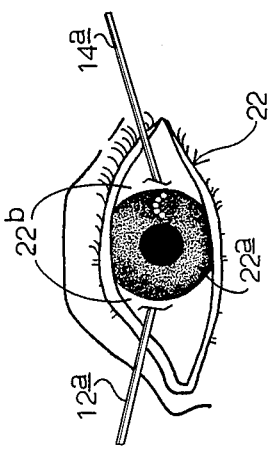

In the preferred embodiment of the invention, each lamp L1 is selectively driven on at a 3 W power level, thereby producing a 30 W output when all ten lights in the circular array are on. As illustrated in FIG. 2B, a single, 3 W incandescent light bulb has been found to provide sufficient luminance to be visible on the cornea of the patient's eye in a typical, ambient lighting environment. It will be appreciated that the wattage of light bulbs, such as light bulb L1, may be changed, they may be driven at different power levels or their optical characteristics may be changed, e.g. by the addition of a rear reflector or lens cover, to produce a higher luminous efficacy or a higher luminous intensity light array. It has been demonstrated that an illuminance of approximately 0.46 lx (15 cd at 10 cm) may be achieved—and is believed to be visible and resolvable on the cornea in the region of the iris over a typical range of ambient lighting conditions—when operating an incandescent bulb having an integral lens at approximately 2 V and 250 mA. A 10 segment light emitting diode (LED) array 54 optionally is provided on the rear cover of display housing 34a, with the LEDs' cathodes each being connected to a corresponding one of driver 48 outputs D1 through D10, and with the LEDs' anodes connected in parallel, via the closure of switch S1, to 13.8 V. The LED array may be used as a trouble-shooting device, as the individual bars in the 10 segment array will reflect the state of corresponding inputs D1 through D10 and should correspond with the on/off state of lights, such as light L1. Ten segment LED array 54 also may be used by an assistant, independently monitoring the vacuum pressure in line 26 while holding or positioning display head 34b.

Figure 4:
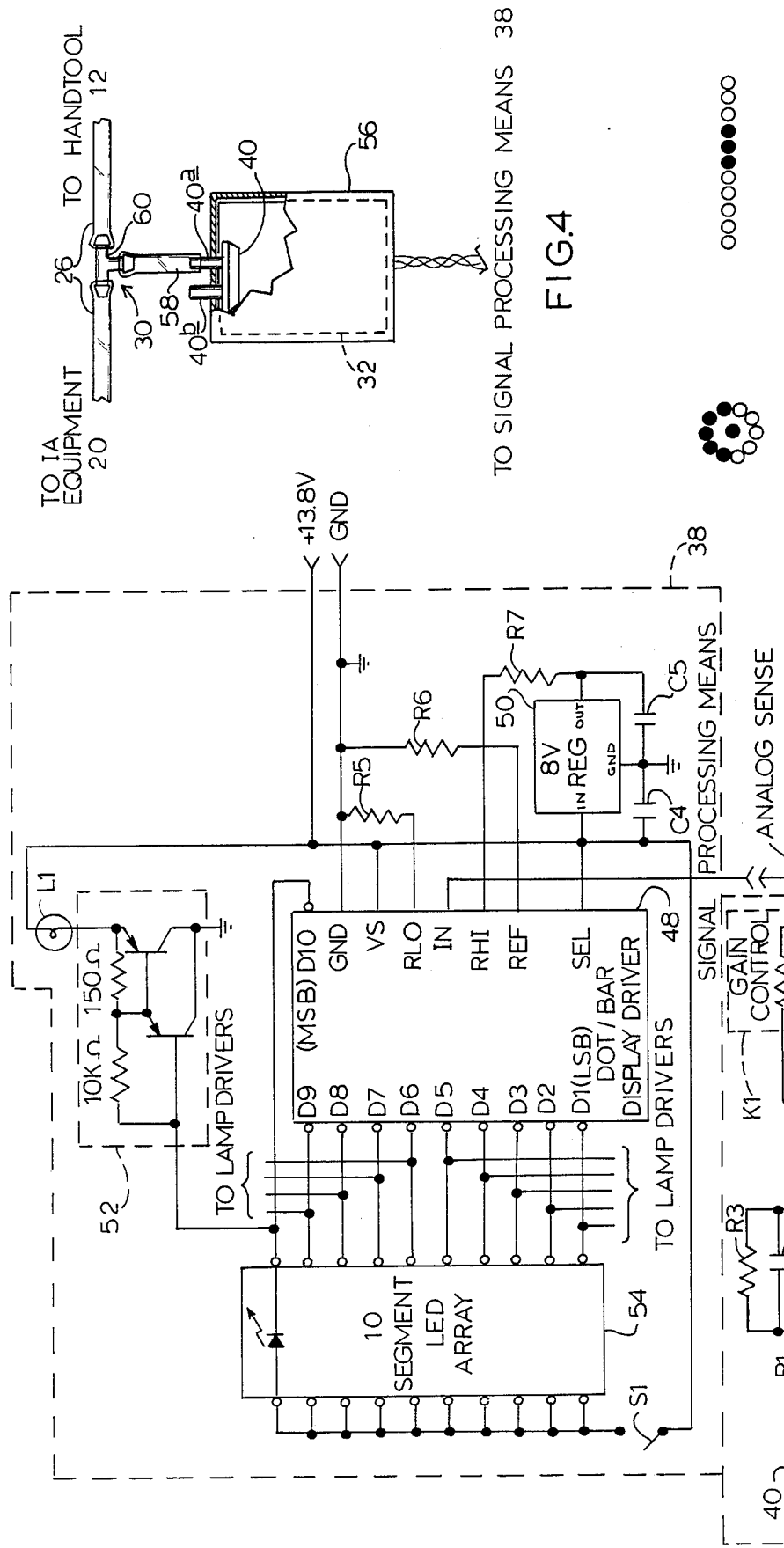
FIG. 4 shows the pneumatic/hydraulic interconnections between conventional equipment and the apparatus of the present invention.
Figure 4:
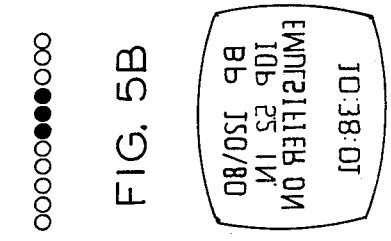

Turning now to FIG. 4, the pneumatic/hydraulic interconnections between the novel apparatus of the present invention and conventional equipment are briefly described. Signal conditioner 32 is shown in dashed outline within a housing 56. The front cover of housing 56 is shown in cutaway view to expose circuit board-mounted pressure transducer 40 in edge view, the transducer having differential ports 40a, 40b extending through holes in the top sidewall of housing 56. A short length of flexible tubing 58 is shown tightly fitted over the open end of vacuum port 40a. The other end of tubing 58 is snugly fitted over the vertical leg of a "T" section coupling member 60, which permits fluid communication among its three ports, the remaining two of which are connected between cut and separated ends of vacuum line 26. It will be appreciated that pressure port 40b similarly may be connected, for example, to pressure line 28 if it is desired instead to image the pressure differential between lines 26, 28.

The means shown in FIG. 4 of interconnecting conventional equipment, by tapping an existing vacuum or pressure line with pressure sensing means, or saline solution-compatible pressure transducer 40 and the associated circuitry of signal conditioner 32, is believe optimally to permit its use in both pneumatic and hydraulic applications, e.g. dry or wet systems This is because the generally vertical orientation of ports 40a, 40b, tubing 58 and "T" section coupling member 60 permit any necessary "bleeding" of bubbles that otherwise might interfere with accurate pressure sensing The straightforwardly available tubing and coupling members shown in the preferred embodiment also are believed to enable the maintenance of the components of the system in a hygienic condition, as the individual parts easily may removed for autoclaving or other cleansing processes. Thus, contamination of the patient's eye may be prevented even if "back-wash" of fluid into an intraocular chamber should occur during a surgical procedure.

Referring briefly again to FIG. 3, the adjustment of GAIN CONTROL and CENTERING CONTROL potentiometers K1, K2 will be described. For a positive vacuum monitoring system, in which the on condition of any light indicates a positive vacuum in line 26, the following adjustments should be made. With vacuum at a minimum, as determined, for example, by meter 20c (refer to FIG. 1), adjust CENTERING CONTROL potentiometer K2 until a single element of the light array becomes visible Set the vacuum to maximum, and then adjust GAIN CONTROL potentiometer K1 until the final light in the array becomes visible Repeat as necessary. If it is desired to have the light array represent positive and negative vacuum, as, for example, when pressure port 40b of transducer 40 is connected to pressure line 28, thereby to measure pressure differential between the aspiration and irrigation lines, the following adjustments should be made. With vacuum at a minimum, adjust CENTERING CONTROL potentiometer K2 until the fifth light in the array is visible Then with vacuum at a maximum, adjust GAIN CONTROL potentiometer K1 until the last light in the array is visible. Repeat as necessary.

Turning finally to FIG. 5, a variety of alternative imaging patterns and techniques are described from what will be understood to be a 'patient's-eye' view. FIG. 5A shows a light array akin to that of the preferred embodiment, but having a centrally located, eleventh light element. The eleventh element may be used, for example, to assist the surgeon in locating the imaging pattern on cornea 22a. In that application, the central, or focal, element would always be on, while the remaining elements might be modulated in accordance with the preferred embodiment described above. Such a central element alternatively might be visibly cycled on and off to indicate that the emulsifier is operating.

Figure 5A:
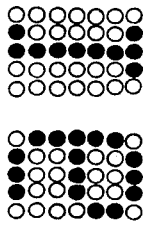
FIGS. 5A-5D shows a series of proposed modifications to the preferred imaging pattern.
Figure 5B:
Figure 5C:
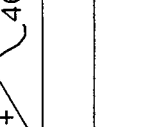

FIG. 5B illustrates a modification to the preferred, circularly arrayed display embodiment, in which instead a linear array of eleven light elements is shown In such an array, the central element continuously might be on, thereby providing a point of reference, for example, from which successive elements on one side thereof progressively are turned on to indicate an increasing vacuum level, and from which successive elements on the opposite side thereof progressively are turned on to indicate an increasing pressure level The central light then might represent a predetermined baseline pressure level, e g., 100 kPa (one atmospheric pressure) or a normal intraocular pressure positive and negative deviations from which are graphically represented As in the proposed modification illustrated in FIG. 5A, the central element of the linear array in FIG. 5B may be cycled on and off at a visible rate, thereby to indicate the on/off condition of the ultrasonic emulsifier.

Referring still to FIG. 5, it will be appreciated that the images illustrated therein, when reflected off of the cornea of the patient's eye, are perceived by the surgeon as "mirror images" and may, depending upon the relative positions of display head 34a, the patient and the surgeon, be reversed both left-to-right and top-to-bottom (as would be the case shown in FIG. 1). It will also be appreciated that the images visible on the cornea are somewhat curved by its convex shape. Thus, the linear array of FIG. 5B would appear as a slightly curved array of light spots Notwithstanding this seeming limitation, it is believed that alphanumeric images, as well as graphic images, commend themselves to use in accordance with the present invention. Illustrative is the two digit, 5×7 dot matrix display of FIG. 5C, wherein a mirror image of the numeric value "16" indicates that the vacuum (or pressure) level being supplied by IA equipment 20 is 16 inches of mercury. Myriad alphabetic or numeric data may be coded in such a display.

Figure 5D:
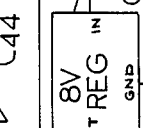

FIG. 5D shows the face of a "projection" tube which, suitably driven and controlled by well-known computer and software means, may display virtually unlimited information. The tube is pictured as simultaneously displaying the patient's blood pressure ("BP 120/80"), the affected eye's intraocular pressure ("IOP 5.2 IN."), the condition of the emulsifier ("ON") and the elapsed time for the current procedure in minutes, seconds and hundreths of seconds ("10:38:01"). Such tubes are capable of providing very high luminescence and thus lend themselves to highly visible, corneal imaging Thus, while graphic imaging patterns have been described as preferred, it will be appreciated that, within the spirit of the invention, an almost infinite variety of data ma be made available perpetually to the surgeon, subject only to limitations including the physical size of the patient's eye, the luminescence of the light array and the ability of the surgeon visually to resolve the pattern and mentally to interpret it in accordance with defined conventions or linguistic standards The preferred method of the invention now may be understood, based upon an understanding of the preferred embodiment of the invention The improvement to an ophthalmic procedure in which a surgeon performs surgery on a patient's eye and data related to the surgery are monitored by external equipment involves reflecting an image, which is interpretable by the surgeon as indicative of the data, off of a visible region of the patient's eye for visual monitoring by the surgeon. In the preferred embodiment, the image is produced by the cooperation of tap 30, signal conditioner 32, signal processing means 38, and circularly arrayed plural element light array 34b. The image may be produced by modulating a light source, e g., plural element light array 34b, with data representing, e.g. the vacuum level within vacuum line 26 and/or the output of ultrasonic detection means, thereby to produce a visible image interpretable by the surgeon as indicative of the data, and by positioning the modulated light source, e.g. display head 34a, relative to the surgeon and the patient's eye such that the image visibly is reflected off of a visible region of the patient's eye for data monitoring by the surgeon More particularly, responsive to a surgical procedure involving the patient's eye, the apparatus of the present invention enables sensing at least one predefined condition (e.g. vacuum level in vacuum line 26) responsive to the surgical procedure (e.g. depression of foot pedal 18) to produce a signal (e.g. ANALOG SENSE) representative thereof; processing the signal (e.g. by signal processing means 38) to produce a visible image interpretable by the surgeon as being indicative of the condition; and positioning the image relative to the surgeon and the patient's eye such that the image is visibly reflected off of a visible region thereof for monitoring by the surgeon. The preferred method of the present invention has been found to be particularly useful with equipment capable of aspirating and/or irrigating the patient's intraocular chamber by communicating therewith a lower (vacuum) and/or higher (pressure) condition than the intraocular pressure, thereby to provide the surgeon with feedback regarding the pressure condition.

Further to the preferred method, the signal processing includes intensity modulating the light source with the signal to produce the image The signal processing is performed by digitizing the signal to produce a ten bit binary code the ten bits of which are used to modulate a circularly arrayed, ten element light source The light source may be intensity modulated with the signal to produce an image in which each element is on or off, or therebetween, i.e. one or more light elements may be intensity modulated to convey information, in serial or parallel, in a variety of ways including digital or analog amplitude modulation (AM), time or pulse interval modulation (PIM) r any other of a variety of human interpretable, spatio-temporal modulation or coding techniques. As proposed in a modification to the preferred method, the processing may include color modulating various elements of the light source. It will be appreciated by those skilled in the art that a combination of intensity and color modulation is contemplated hereby, and is within the spirit of the invention.

Finally, a modification to the preferred method of the invention addresses more general applications in which it is believed to be useful. In the surgical or therapeutic treatment of a patient, a method which enables the monitoring, of data related to the treatment, by a medical practitioner involves (1) modulating a light source with the data to produce a visible image interpretable by the practitioner as indicative of the data, and (2) visibly projecting the image onto a visible region of the patient's body for data monitoring by the practitioner. Such projecting can be accomplished, within the spirit and teachings of the present invention, by providing one or more light sources capable of relatively nondiffuse projection from a display head to any desired, visible region of the patient's body As in the preferred embodiment and method of the present invention, the light source may be luminance or color modulated, or both Indeed, the main difference between the proposed modification and the preferred method described above is that, in a projecting heads up display system, the light source should be relatively nondiffuse, whether by using collimated light elements and/or optical transmission means, or by controlling the distance between the display head and the projection surface (which may be relatively nonreflective) of the patient's body (or both), thereby rendering the projected image as readily discernible and interpretable under typical ambient lighting conditions as is the reflected image By the use of either method, and by properly positioning or directing the light source, a visible, coded display may be rendered in a region of the patient's body proximate to the focus of the medical practitioner's attention, thereby enabling perpetual data monitoring and feedback.

Accordingly, while a preferred embodiment of the invention and a preferred method of practicing the invention, including proposed modifications thereto, have been described, it will be appreciated that further modifications are possible that come within the scope of the invention.

It is claimed and desired to secure by Letters Patent:

1. In an ophthalmic procedure wherein a surgeon performs surgery on a patient's eye and data related to the surgery are monitored by external equipment, the improvement of:
   reflecting an image, which is interpretable by the surgeon as indicative of the data, off of a visible region of the patient's eye for visual monitoring by the surgeon.

2. For use in ophthalmic surgery, a method which enables the monitoring of data related to the surgery by a surgeon performing surgery on a patient's eye, comprising:
   modulating a light source with the data to produce a visible image interpretable by the surgeon as indicative of the data, and
   positioning the modulated light source relative to the surgeon and the patient's eye such that the image visibly is reflected off of a visible region of the patient's eye for data monitoring by the surgeon.

3. For use in ophthalmic surgery, a method for providing a surgeon with feedback regarding conditions responsive to a surgical procedure involving a patient's eye, comprising:
   sensing at least one predefined condition responsive to the surgical procedure to produce a signal which is representative of the condition;
   processing the signal to produce a visible image interpretable by the surgeon as being indicative of the condition; and
   positioning the image relative to the surgeon and the patient's eye such that the image visibly is reflected off of a visible region of the patient's eye for monitoring by the surgeon.

4. For use in ophthalmic surgery with equipment capable of aspirating or irrigating a patient's intraocular chamber by fluid communicating therewith a lower or higher pressure condition than the pressure within the chamber, a method for providing a surgeon with feedback regarding the pressure condition, comprising:
   sensing the pressure condition to produce a signal which is representative of the pressure condition;
   processing the signal to produce a visible image interpretable by the surgeon as being indicative of the pressure condition; and
   positioning the image relative to the surgeon and the patient's eye such that the image visibly is reflected off of a visible region of the patient's eye for monitoring by the surgeon.

5. The method of claim 4, wherein the processing includes luminance modulating a light source with the signal to produce the image.

6. The method of claim 4, wherein the processing includes digitizing the signal to produce a multi-bit binary code the bits of which are used to modulate a plural element light source to produce the image.

7. The method of claim 4, wherein the processing includes intensity modulating a generally circularly arrayed, plural element light source with the signal to produce the image.

8. The method of claim 4, wherein the processing includes color modulating a light source with the signal to produce the image.

9. For use with ophthalmic surgery equipment capable of aspirating or irrigating a patient's intraocular chamber by fluid communicating therewith a lower or higher pressure condition than the pressure within the chamber, apparatus for providing a surgeon with feedback regarding the pressure condition, comprising:
   means for sensing the pressure condition to produce a signal which is representative of the pressure condition;
   means for processing the signal to produce a visible image interpretable by the surgeon as being indicative of the pressure condition, and
   means for positioning the image relative to the surgeon and the patient's eye such that the image visibly is reflected off of a visible region of the patient's eye for monitoring by the surgeon.

* * * * *